United States Patent [19]

Abou-Gharbia et al.

[11] Patent Number: 4,797,489

[45] Date of Patent: Jan. 10, 1989

[54] ADAMANTYL- AND FLUORENYL-ARYLPIPERAZINES AND -ARYLPIPERIDINES

[75] Inventors: Magid A. Abou-Gharbia, Wilmington, Del.; Gary P. Stack, Merion; John P. Yardley, Gulph Mills, both of Pa.

[73] Assignee: American Home Products Corp., New York, N.Y.

[21] Appl. No.: 127,740

[22] Filed: Dec. 2, 1987

[51] Int. Cl.$^4$ ............................................. C07D 295/14
[52] U.S. Cl. ...................... 544/331; 544/238; 544/322; 544/328; 544/396; 546/221; 546/239
[58] Field of Search ............... 544/238, 322, 328, 331, 544/396; 546/221, 239

[56] References Cited

U.S. PATENT DOCUMENTS 3,873,583 3/1975 Walz et al. ........................ 546/239
4,202,898 5/1980 Depoortere ....................... 544/394

FOREIGN PATENT DOCUMENTS 375053 5/1971 Netherlands ..................... 544/394

Primary Examiner—Mary C. Lee
Assistant Examiner—Kurt G. Briscoe
Attorney, Agent, or Firm—Richard K. Jackson

[57] ABSTRACT

The compounds

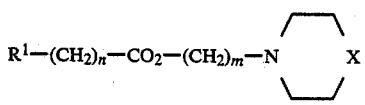

wherein
R$^1$ is 1-adamantyl, 3-methyl-1-adamantyl, 9-fluorenyl or 1-fluorenyl;
n is 0 or 1;
m is 1, 2, 3, 4 or 5; and X is

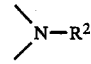

where R$^2$ is phenyl, benzyl, pyridinyl, pyrimidinyl, pyrazinyl or substituted phenyl or benzyl in which the substituent is alkyl of 1 to 6 carbon atoms, alkoxy of 1 to 6 carbon atoms, halo, cyano, nitro or trifluoromethyl,

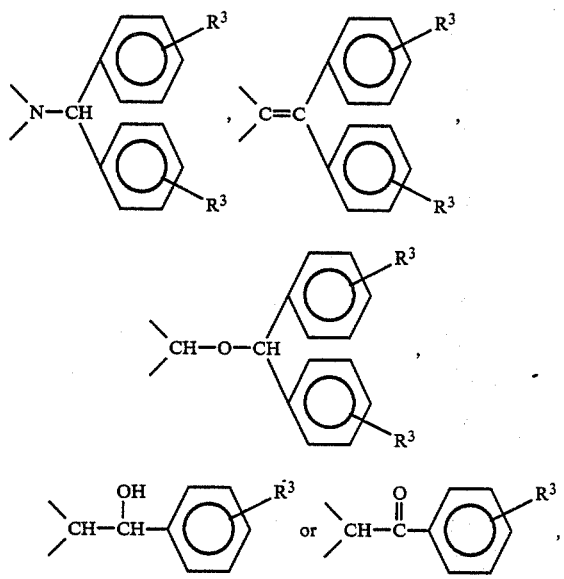

where R$^3$ is hydrogen, alkyl of 1 to 6 carbon atoms, alkoxy of 1 to 6 carbon atoms, halo, cyano or nitro;

or pharmaceutically acceptable salts thereof are useful antidepressant and/or anxiolytic agents.

14 Claims, No Drawings

ADAMANTYL- AND FLUORENYL-ARYLPIPERAZINES AND -ARYLPIPERIDINES

BACKGROUND OF THE INVENTION

Derwent Abstract 85-000957/01 of German Application No. 3,321,969 discloses 1-pyrimidyl-4-substituted piperazine derivative which possess a broad variety of CNS activity including anxiolytic and antidepressant properties. Netherlands Pat. No. 7,017,031 discloses 8-(heteroarylpiperazinylalkyl)-8-azaspiro[4,5]decane-7,9-diones as tranquilizers. U.S. Pat. No. 4,640,921 (Derwent Abstract 87-049798/07 discloses the use of the buspirones of the Netherlands patent in the treatment of sexual dysfunction in anxious patients. The anxiolytic activity of buspirone-like compounds has been attributed to their selective activation of a serotonin (5-hydroxytryptamine; 5-HT) subtype receptor designated the $5-HT_{1A}$ receptor. U.S. Pat. No. 4,202,898 discloses the treatment of anxiety and depression with aromatically substituted piperazine derivatives. $5-HT_2$ antagonists, such as Ritanserin, lack $5-HT_{1A}$ affinity but demonstrated clinical efficacy as anxiolytic-antidepressant agents (Barone et al., Drug Clin. Pharm., 20, 770, 1986).

DESCRIPTION OF THE INVENTION

In accordance with this invention there is provided a group of novel compounds possessing anxiolytic, antidepressant and in some instances antipsychotic activity. The compounds of this invention are of the following structural formula:

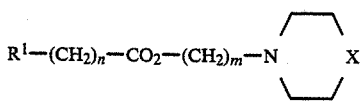

wherein
$R^1$ is 1-adamantyl, 3-methyl-1-adamantyl, 9-fluorenyl or 1-fluorenyl;
n is 0 or 1;
m is 1, 2, 3, 4 or 5; and
X is

where $R^2$ is phenyl, benzyl, pyridinyl, pyrimidinyl, pyrazinyl, or substituted phenyl or benzyl in which the substituent is alkyl of 1 to 6 carbon atoms, alkoxy of 1 to 6 carbon atoms, halo, cyano, nitro or trifluoromethyl,

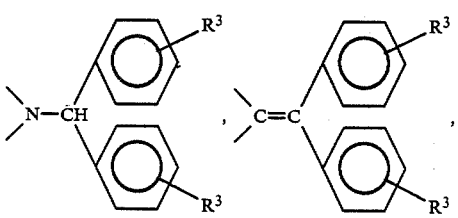

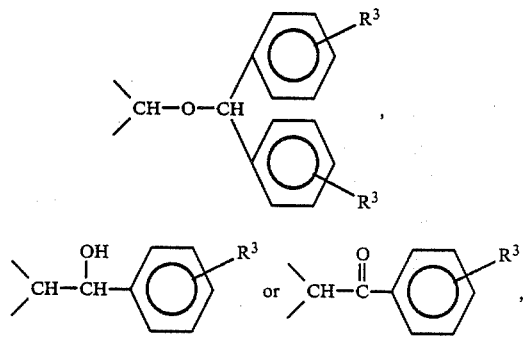

where $R^3$ is hydrogen, alkyl of 1 to 6 carbon atoms, alkoxy of 1 to 6 carbon atoms, halo, cyano or nitro;
or a pharmaceutically acceptable salt thereof.

The pharmaceutically acceptable salts are conveniently derived by conventional means from such acids as hydrochloric, hydrobromic, sulfuric, phosphoric, methane sulfonic, nitric, p-toluene sulfonic, acetic, citric, maleic, succinic acid, and the like. The halogens embraced by the term halo are chlorine, bromine, iodine and fluorine, preferably chlorine, bromine or fluorine.

The compounds of this invention may be prepared by a variety of synthetic routes using conventional methods. For instance, 1-adamantanecarboxylic acid halide, 3-methyl-1-adamantanecarboxylic halide, 1-fluorenylcarboxylic acid halide or 9-fluorenylcarboxylic acid halide may be conveniently reacted with the appropriately substituted

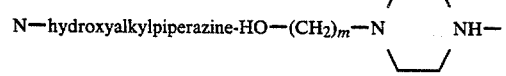

in $CH_2Cl_2$ and the presence of a suitable base, such as triethylamine, to obtain the desired intermediate or final product or, alternatively, the acid halides may be reacted with the desired hydroxyhaloalkane -HO-$(CH_2)_m$-Br- in $CH_2Cl_2$ and the presence of a suitable base, such as triethylamine, followed by reacting the intermediate bromoalkylester with the desired aromatically or heteroaromatically substituted piperazine or piperidine intermediate.

The following examples illustrate, without limitation, the specific methods employed in production of a representative number of compounds embraced by this invention.

EXAMPLE 1.

Tricyclo[$3.3.1.1^{3,7}$]decane-1-carboxylic acid 3-[4-(3-chlorophenyl)-1-piperazinyl]propyl ester To a stirred solution of 3-bromopropanol (5.56 g, 0.04 mol) in 50 mL of methylene chloride, adamantane-1-carboxylic acid chloride (5.6 g, 0.02 mol) and triethylamine (4 g, 0.04 mol) were added. The reaction mixture was stirred at room temperature overnight, the methylene chloride was washed with water, dried over anhydrous $Na_2SO_4$ and removed under reduced pressure to afford 12 g of the intermediate adamantane-1-carboxylic acid bromopropyl ester. The title compound was prepared by stirring 4-(3-chlorophenyl)-1-piperazine (2.7 g, 0.011 mol), adamantane-1-carboxylic acid bromopropyl ester (3.5 g, 0.011 mol) and triethylamine (2.5 g, 0.025 mol) in 50 mL of $CH_2Cl_2$ for 24 hours. The methylene chloride was washed with water, dried (anhydrous $Na_2SO_4$) and removed under reduced pressure. The remaining residue was subjected to preparative HPLC over silica gel using ethylacetate as the eluent and the desired product (TLC $R_f=0.6$ in 30% methanol/ethylacetate) was separated and converted to the dihydrochloride salt with ethanolic HCl (1 g, 20% yield), mp. 220°–222° C.

Elemental Analysis for $C_{24}H_{33}N_2ClO_2.HCl$: Calc'd: C, 58.84; H, 7.15, N, 5.72. Found: C, 59.00; H, 7.03; N, 5.55.

EXAMPLE 2

Tricyclo[3.3.1.1$^{3,7}$]decane-1-carboxylic acid 2-[4-(2-pyrimidinyl)-1-piperazinyl]ethyl ester To a stirred solution of [4-(2-pyrimidinyl)-piperazino]ethanol (3.7 g, 0.017 mol) in 50 mL of methylene chloride, adamantane-1-carboxylic acid chloride (5 g, 0.018 mol) and triethylamine (2 g, 0.02 mol) were added. Stirring was continued at room temperature overnight. The methylene chloride was washed with water, dried over anhydrous sodium sulfate and evaporated under reduced pressure. The remaining residue was subjected to preparative HPLC as in Example 1. In repeated preparations, the residue was dissolved in ethylacetate (10 mL) and subjected to flash chromatography using a 9 inch column of silica gel with ethylacetate as the eluent. The title compound (TLC $R_f=0.63$ in 30% methanol/ethylacetate system) was separated and converted to the hydrochloride salt with ethanolic HCl (3 g, 43% yield), mp. 232°–235° C.

Elemental Analysis for $C_{21}H_{30}N_4O_2.HCl$ Calc'd: C, 61.92; H, 7.63; N, 13.76. Found: C, 61.38; H, 7.51; N, 14.10.

EXAMPLE 3

Tricyclo[3.3.1.1$^{3,7}$]decane-1-carboxylic acid 3-[4-(2-methoxyphenyl)-1-piperazinyl]propyl ester To a stirred solution of [4-(2-methoxyphenyl)-piperazino]ethanol (3.7 g, 0.015 mol) in 50 mL of methylene chloride, adamantane-1-carboxylic acid chloride (5 g, 0.018 mol) and triethylamine (2 g, 0.02 mol) werre added. Stirring was continued at room temperature overnight. The methylene chloride was washed with water, dried over anhydrous sodium sulfate and evaporated under reduced pressure. The remaining residue was subjected to preparative HPLC (as in Example 1). In repeated preparations, the residue was dissolved in ethylacetate (10 mL) and subjected to flash chromatography using a 9 inch column of silica gel and ethylacetate as the eluent. The title compound (TLC $R_f=0.65$ in 30% methanol/ethylacetate system) was separated and converted to the dihydrochloride salt with ethanolic HCl (4 g, 55% yield); mp. 212°–213° C.

Elemental Analysis for $C_{25}H_{36}N_2O_3.2$ HCl: Calc'd: C, 61.85; H, 7.83; N, 5.77. Found: C, 61.55; H, 7.95; N, 5.61.

EXAMPLE 4

3-Methyltricyclo[3.3.1.1$^{3,7}$]decane-1-acetic acid 2-[4-(2-pyrimidinyl)-1-piperazinyl]ethyl ester To a stirred solution of [4-(2-pyrimidinyl)-piperazino]ethanol (3.73 g, 0.017 mol) in 50 mL of methylene chloride, 3-methyladamantane-1-acetic acid chloride (4 g, 0.018 mol) and triethylamine (5 g, 0.05 mol) were added. Stirring was continued at room temperature overnight. The methylene chloride was washed with water, dried over anhydrous sodium sulfate and evaporated under reduced pressure. The remaining residue was subjected to preparative HPLC (as in Example 1) using ethylacetate as the eluent to afford the title compound as the free base, which was converted to the dihydrochloride salt with ethanolic HCl (2.9 g, 33% yield); mp 202°–206° C.

Elemental Analysis for $C_{23}H_{34}N_4O_2.2$ $HCl.H_2O$: Calc'd: C, 56.43; H, 7.82; N, 11.44; Cl, 14.40. Found: C, 56.08; H, 7.53; N, 11.39; Cl, 14.32.

EXAMPLE 5

9H-Fluorene-1-carboxylic acid 2-[4-(2-methoxyphenyl)-1-piperazinyl]ethyl ester

To a stirred solution of 2-bromoethanol (3.3 g, 0.026 mol) in 50 mL of methylene chloride, fluorene-1-carboxylic acid chloride (6.0 g, 0.026 mol) and triethylamine (5 g, 0.05 mol) were added. The reaction mixture was stirred at room temperature overnight, the methylene chloride was washed with water, dried over anhydrous $Na_2SO_4$ and removed under reduced pressure to afford 7 g of the intermediate fluorene-1-carboxylic acid bromoethyl ester. The title compound was prepared by stirring 4-(2-methoxyphenyl)-1-piperazine (2.1 g, 0.011 mol), fluorene-1-carboxylic acid bromoethyl ester (3.5 g, 0.011 mol) and triethylamine (1.5 g, 0.015 mol) in 50 mL of $CH_2Cl_2$ for 24 hours. The methylene chloride was washed with water, dried (anhydrous $Na_2SO_4$) and removed under reduced pressure. The remaining residue was subjected to preparative HPLC using ethylacetate as the eluent (as in Example 1) and the desired product was separated and converted to the dihydrochloride salt with ethanolic HCl (2 g, 35% yield), mp. 213°–215° C.

Elemental Analysis for $C_{27}H_{28}N_2O_3.2$ $HCl.H_2O$: Calc'd: C, 62.43; H, 6.16; N, 5.39. Found: C, 62.73; H, 6.24; N, 5.30.

EXAMPLE 6

3-Methyltricyclo[3.3.1.1$^{3,7}$]decane-1-acetic acid 3-[4-[3-(trifluoromethyl)phenyl]-1-piperazinyl]propyl ester To a stirred solution of [4-(3-trifluoromethylphenyl)-piperazino]-propanol (4.3 g, 0.015 mol) in 50 mL of methylene chloride, 3-methyladamantane-1-acetic acid chloride (3.4 g, 0.015 mol) and triethylamine (2 g, 0.02 mol) were added. Stirring was continued at room temperature overnight. The methylene chloride was washed with water, dried over anhydrous sodium sulfate and evaporated under reduced pressure. The remaining residue was subjected to preparative HPLC (as in Example 1) using ethylacetate as the eluent to afford the title compound as the free base which was converted to the hydrochloride salt with ethanolic HCl (2.9 g, 38% yield); mp. 177°–180° C.

Elemental Analysis for $C_{27}H_{37}F_3N_2O_2.HCl$: Calc'd: C, 62.97; H, 7.39; N, 5.44. Found: C, 62.70; H, 6.96; N, 5.29.

EXAMPLE 7

Tricyclo[3.3.1.1³,⁷]decane-1-carboxylic acid 3-[4-(2-pyrimidinyl)-1-piperazinyl]propyl ester To a stirred solution of [4-(2-pyrimidinyl)piperazino]propanol (3.9 g, 0.017 mol) in 50 mL of methylene chloride, adamantane-1-carboxylic acid chloride (5 g, 0.017 mol) and triethylamine (2 g, 0.02 mol) were added. Stirring was continued at room temperature overnight. The methylene chloride was washed with water, dried over anhydrous sodium sulfate and evaporated under reduced pressure. The remaining residue was subjected to preparative HPLC (as in Example 1). In repeated preparations, the residue was dissolved in ethylacetate (10 mL) and subjected to flash chromatography using a 9 inch column of silica gel and ethylacetate as the eluent. The title compound (TLC $R_f$=0.67 in 30% methanol/ethylacetate system) was separated and converted to the dihydrochloride salt with ethanolic HCl (3 g, 38% yield); mp. 209°–211° C.

Elemental Analysis for $C_{22}H_{32}N_4O_2.2$ HCl.1/2 $H_2O$: Calc'd: C, 56.65; H, 7.51; N, 12.01. Found: C, 56.51; H, 7.37; N, 12.04.

EXAMPLE 8

9H-Fluorene-1-carboxylic acid 2-[4-(3-chlorophenyl)-1-piperazinyl]ethyl ester

To a stirred solution of 2-bromoethanol (3.3 g, 0.026 mol) in 50 mL of methylene chloride, fluorene-1-carboxylic acid chloride (6 g, 0.026 mol) and triethylamine (5 g, 0.05 mol) were added. The reaction mixture was stirred at room temperature overnight. The methylene chloride was washed with water, dried over anhydrous $Na_2SO_4$ and removed under reduced pressure to afford 7 g of the intermediate fluorene-1-carboxylic acid bromoethyl ester. The title compound was prepared by stirring 4-(3-chlorophenyl)piperazine (2.6 g, 0.011 mol), fluorene-1-carboxylic acid bromoethyl ester (3.5 g, 0.011 mol) and triethylamine (2.5 g, 0.025 mol) in 50 mL of $CH_2Cl_2$ for 24 hours. The methylene chloride was washed with water, dried (anhydrous $Na_2SO_4$) and removed under reduced pressure. The remaining residue was subjected to preparative HPLC over silica gel using ethylacetate as the eluent and the desired product (TLC $R_f$=0.68 in 30% methanol/ethylacetate system) was separated and converted to the dihydrochloride salt with ethanolic HCl (1.8 g, 31% yield), mp. 215°–217° C.

Elemental Analysis for $C_{26}H_{25}N_2ClO_2.2$ HCl.$H_2O$: Calc'd: C, 59.60; H, 5.54; N, 5.34. Found: C, 59.72; H, 5.56; N, 4.98.

EXAMPLE 9

Tricyclo[3.3.1.1³,⁷]decane-1-carboxylic acid 3-[4-[bis(4-fluorophenyl)methylene]-1-piperidinyl]propyl ester To a stirred solution of 3-bromopropanol (5.5 g, 0.04 mol) in 50 mL of methylene chloride, adamantane-1-carboxylic acid chloride (5.6 g, 0.02 mol) and triethylamine (4 g, 0.04 mol) were added. The reaction mixture was stirred at room temperature overnight, the methylene chloride was washed with water, dried over anhydrous $Na_2SO_4$ and removed under reduced pressure to afford 12 g of the intermediate adamantane-1-carboxylic acid bromopropyl ester. The title compound was prepared by stirring 4-[bis(4-fluorophenyl)-methylene]piperidine (2 g, 0.07 mol), adamantane-1-carboxylic acid bromo-propyl ester (2.1 g, 0.007 mol) and triethylamine (1 g, 0.01 mol) in 50 mL of $CH_2Cl_2$ for 24 hours. The methylene chloride was washed with water, dried (anhydrous $Na_2SO_4$) and removed under reduced pressure. The remaining residue was subjected to preparative HPLC over silica gel using ethylacetate as the eluent and the desired product (TLC $R_f$=0.7 in 30% ethanol/ethylacetate system) was separated and converted to the hydrochloride salt (0.6 g, 16% yield), mp. 267°–269° C.

Elemental Analysis for $C_{32}H_{37}NF_2O_2.HCl$: Calc'd: C, 70.91; H, 7.02; N, 2.58. Found: C, 71.29; H, 7.11; N, 2.30.

EXAMPLE 10

Tricyclo[3.3.1.1³,⁷]decane-1-carboxylic acid [2-[4-(2-cyanophenyl)-1-piperazinyl]ethyl]ester 2-Fluorobenzonitrile (6.0 g, 50 mmoles) and 1-(2-hydroxyethyl)-piperazine (6.5 g, 50 mmoles) were combined in 500 mL of dimethylformamide and heated at 80° C. under $N_2$ for 24 hours. After cooling, the solvent was removed in vacuum and the crude 1-(2-hydroxyethyl)-4-(2-cyanophenyl)piperazine thus produced was used without purification. 2.3 Grams (10 mmole) of the crude 1-(2-hydroxyethyl)-4-(2-cyanophenyl)piperazine was dissolved in 100 mL of $CH_2Cl_2$ and 1.3 g (10 mmole) of diisopropyl ethylamine was added, followed by addition of 2.0 g (10 mmole) of 1-adamantanecarbonyl chloride. The mixture was stirred at room temperature for 3 hours, washed with saturated $NaHCO_3$ solution, saturated brine, dried over $Na_2SO_4$, filtered and concentrated in vacuum. The residue was column chromatographed on 100 g of silica gel with $CHCl_3$ and the product thus obtained was crystallized from isopropanol with the addition of 4N isopropanolic HCl to give 1.1 g of title compound as the monohydrochloride salt, mp. 230°–231° C.

Elemental Analysis for $C_{24}H_{31}N_3O_2.HCl$: Calc'd: C, 67.04; H, 7.50; N, 9.77. Found: C, 66.95; H, 7.28; N, 9.62.

EXAMPLE 11

Tricyclo[3.3.1.1³,⁷]decane-1-carboxylic acid 2-[4-[bis(4-fluorophenyl)methylene]-1-piperidinyl]ethyl ester To a stirred solution of 2-bromoethanol (4.9 g., 0.04 mol) in 50 mL of methylene chloride, adamantane-1-carboxylic acid chloride (5.6 g., 0.02 mol) and triethylamine (4 g., 0.04 mol) were added. The reaction mixture was stirred at room temperature overnight and the methylene chloride was washed with water, dried over anhydrous $Na_2SO_4$ and removed under reduced pressure to afford 12 g. of the intermediate adamantane-1-carboxylic acid bromoethyl ester. The title compound was prepared by stirring 4-[bis(4-fluorophenyl)-methylene]piperidine (2 g., 0.07 mol), adamantane-1-carboxylic acid bromoethyl ester (2.0 g., 0.007 mol) and triethylamine (1 g., 0.01 mol) in 50 mL of $CH_2Cl_2$ for 24 hours. The methylene chloride was washed with water, dried (anhydrous $Na_2SO_4$) and removed under reduced pressure. The remaining residue was subjected to preparative HPLC over silica gel using ethylacetate as the eluent and the desired product (TLC $R_f$=0.75 in 30% ethanol/ethylacetate system) was separated and converted to the hydrochloride salt with ethanolic HCl; mp. 249°–254° C.

Elemental Analysis for $C_{31}H_{35}F_2NO_2 \cdot HCl$: Calc'd: C, 70.50; H, 6.87; N, 2.65. Found: C, 70.56; H, 7.07; N, 2.80.

EXAMPLE 12

Tricyclo[3.3.1.1$^{3,7}$]decane-3-methyl-1-acetic acid 2-[4-[bis(4-fluorophenyl)methylene]-1-piperidinyl]ethyl ester To a stirred solution of 2-bromoethanol (4.9 g, 0.04 mol) in 50 mL of methylene chloride, 3-methyladamantane-1-acetic acid chloride (6.1 g., 0.02 mol) and triethylamine (4 g., 0.04 mol) were added. The reaction mixture was stirred at room temperature overnight. The methylene chloride was washed with water, dried over anhydrous $Na_2SO_4$ and removed under reduced pressure to afford 12 g. of the intermediate adamantane-1-acetic acid bromoethyl ester. The title compound was prepared by stirring 4-[bis(4-fluorophenyl)methylene]-piperidine (2 g., 0.07 mol), adamantane-1-acetic acid bromoethyl ester (2.2 g., 0.007 mol) and triethylamine (1 g., 0.01 mol) in 50 mL of $CH_2Cl_2$ for 24 hours. The methylene chloride was washed with water, dried (anhydrous $Na_2SO_4$) and removed under reduced pressure. The residue was subjected to preparative HPLC over silica gel using ethylacetate as the eluent and the desired product (TLC $R_f = 0.7$ in 30% ethanol/ethylacetate system) was separated and converted to the hydrochloride salt with ethanolic HCL, mp. 208°–209° C.

Elemental Analysis for $C_{33}H_{39}F_2NO_2 \cdot HCl$: Calc'd: C, 71.26; H, 6.83; N, 2.52. Found: C, 71.62; H, 7.12; N, 2.34.

EXAMPLE 13

Tricyclo[3.3.1.1$^{3,7}$]decane-3-methyl-1-acetic acid 2-[4-(4-fluorophenyl)hydroxymethyl]-1-piperidinyl]ethyl ester To a stirred solution of 2-bromoethanol (3.3 g, 0.026 mol) in 50 mL of methylene chloride, 3-methyladamantane-1-acetic acid chloride (6.1 g, 0.02 mol) and triethylamine (5 g., 0.05 mol) were added. The reaction mixture was stirred at room temperature overnight. The methylene chloride was washed with water, dried over anhydrous $Na_2SO_4$ and removed under reduced pressure to afford 7 g. of the intermediate 3-methyladamantane-1-acetic acid bromoethyl ester. The title compound was prepared by stirring 4-[4-fluorophenyl]hydroxymethyl piperidine (4.0 g., 0.016 mol), 3-methyladamantane-1-acetic acid bromoethyl ester (4.6 g., 0.016 mol) and triethylamine (2.5 g., 0.025 mol) in 50 mL of $CH_2Cl_2$ for 24 hours. The methylene chloride was washed with water, dried (anhydrous $Na_2SO_4$) and removed under reduced pressure. The remaining residue was subjected to preparative HPLC over silica gel using ethylacetate as the eluent and the desired product (TLC $R_f = 0.75$ in 30% methanol/ethylacetate system) was separated and converted to the hydrochloride salt with ethanolic HCl, mp. 179°–184° C.

Elemental Analysis for $C_{25}H_{34}FNO_3 \cdot HCl \cdot 5/2\ H_2O$: Calc'd: C, 60.41; H, 8.11; N, 2.82. Found: C, 60.35; H, 7.14; N, 2.89.

The compounds of this invention are antidepressant, anxiolytic agents useful in the treatment of depression and/or anxiety as singular, primary mental problem as well as secondary, attending problems such as sexual dysfunction, senile dementia, and the like. Some of the compounds possess sufficient dopaminergic activity to be useful in treating psychoses such as schizophrenia or paranoia. Examples of compounds with sufficient limbic D$_2$ (dopamine) receptor affinity to be considered to have an antipsychotic parameter are those demonstrating about 80% or more inhibition of $^3$H-spiroperidol binding to limbic brain tissue at 1 $\mu$M concentration of the test compound. The D$_2$ receptor affinity of representative compounds of this invention was determined by a modification of the test procedure of Fields et al., Brain Res. 136, 578 (1977) and Yamamura et al., eds., Neurotransmitter Receptor Binding, Raven Press, N.Y. (1978) as discussed in U.S. Pat. No. 4,636,563. The percentage reduction of $^3$H-spirohaloperidol binding at 1 $\mu$M concentration of test compound is reported, infra, and the inhibition constant (Ki) for the specific test compound is reported where available. Buspirone exhibits an Ki of 78 nM (84% inhibition) of $^3$H-spirohaloperidol binding in this standard test procedure.

The serotoninergic properties of the compounds of this invention were established by the procedure of Hall et al., J. Neurochem. 44, 1685–1696 (1985) by demonstrating that representative compounds exemplified herein displace $^3$H-8-OH DPAT (dipropylaminotetralin) from the 5-HT$_{1A}$ serotonin receptor subtype. The results of this standard pharmacological procedure are reported, infra, as the percent inhibition at 1 nM concentration of test compound or by providing the inhibition constant Ki for the specific test compound where that calculation has been made from appropriate IC$_{50}$ values. Buspirone exhibits an Ki of 10 nM (97% inhibition) in this test procedure.

5-HT$_2$ inhibition of $^3$H-spiroperidol is determined in an analogous manner, employing rat brain cortex homogenate as the receptor tissue, following a modification of Fields et al., ibid; Yamamura et al., ibid; and Creese et al., Eu. J. Pharmacol. 49, 20 (1978).

| Compound | Receptor Binding Ki(nM) or % Inhibition at 1 $\mu$M | | |
|---|---|---|---|
| | 5HT$_{1A}$ | 5HT$_2$ | D$_2$ |
| Example 1 | 80% | | 67% |
| Example 2 | 8.5 nM | | 26% |
| Example 3 | 100% | | 90% |
| Example 4 | 72% | | 39% |
| Example 5 | 100% | | |
| Example 7 | 69% | | 33% |
| Example 8 | 53% | | |
| Example 10 | | | 90% |
| Example 11 | 95% | 98% | 100% |
| Example 12 | | 63% | 36% |
| Buspirone | 10 nM (97%) | | 78 nM (84%) |

In qualitatively evaluating the above data, high affinity values for 5-HT$_{1A}$ receptors correlate (by analogy with buspirone) with anxiolytic-antidepressant activity, while lower values reflect a lesser activity. High affinity values for D$_2$ receptor binding (greater than 80%) begin to show some antipsychotic activity and high affinity for 5-HT$_2$ receptor sites indicate anxiolytic and/or antidepressant activity.

Hence, the compounds of this invention are antidepressant, anxiolytic agents useful in the treatment of depression and in alleviating anxiety and in the case of the products of Examples 3, 10 and 12 they have some meaningful antipsychotic activity which is useful in the treatment of psychoses such as paranoia and schizophrenia. As such, they may be administered to a patient in need thereof, either neat or with a conventional pharmaceutical carrier. The pharmaceutical carrier may be solid or liquid as suitable for oral or parenteral administration.

A solid carrier can include one or more substances which may also act as flavoring agents, lubricants, solubilisers, suspending agents, fillers, glidants, compression aids, binders or tablet-disintegrating agents; it can also be an encapsulating material. In powders the carrier is a finely divided solid which is in admixture with the finely divided active ingredient. In tablets the active ingredient is mixed with a carrier having the necessary compression properties in suitable proportions and compacted in the shape and size desired. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilisers, emulsifiers, buffers, preservatives, sweeteners, flavoring agents, suspending agents, thickening agents, colors, viscosity regulators, stabilisers of osmo-regulators. Suitable examples of liquid carriers for oral and parenteral administration include water (particularly containing additives as above, e.g. cellulose derivatives, preferably sodium carboxymethyl cellulose solution), alcohols (including monohydric alcohols and polyhydric alcohols, e.g., glycols) and their derivatives, and oils (e.g. fractionated coconut oil and arachis oil). For parenteral administration the carrier can also be an oil ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by, for example, intramuscular, intraperitoneal or subcutaneous injection. Sterile solutions can also be administered intravenously. When the compound is orally active it can be administered orally either in liquid or solid composition form.

Preferably the pharmaceutical composition is in unit dosage form, e.g. as tablets or capsules. In such form, the composition is subdivided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or table itself, or it can be the appropriate number of any such compositions in package form.

The dosage to be used in the treatment of anxiety, depression or psychoses must be subjectively determined by the attending physician. The variables involved include the specific state of depression, anxiety or psychoses and the size, age and response pattern of the patient.

What is claimed is:

1. A compound of the formula:

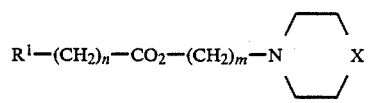

wherein
$R^1$ is 1-adamantyl, 3-methyl-1-adamantyl, 9-fluorenyl or 1-fluorenyl;
$n$ is 0 or 1;
$m$ is 1, 2, 3, 4 or 5; and
$X$ is

where $R^2$ is phenyl, benzyl, pyridinyl, pyrimidinyl, pyrazinyl, or substituted phenyl or benzyl in which the substituent is alkyl of 1 to 6 carbon atoms, alkoxy of 1 to 6 carbon atoms, halo, cyano, nitro or trifluoromethyl,

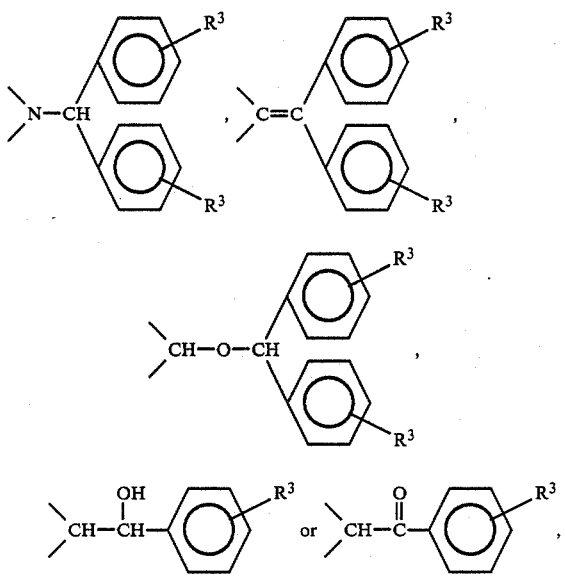

where $R^3$ is hydrogen, alkyl of 1 to 6 carbon atoms, alkoxy of 1 to 6 carbon atoms, halo, cyano or nitro;
or a pharmaceutically acceptable salt thereof.

2. The compound of claim 1 which is tricyclo[3.3.1.1$^{3,7}$]-decane-1-carboxylic acid 3-[4-(3-chlorophenyl-1-piperazinyl]propyl ester, or a pharmaceutically acceptable salt thereof.

3. The compound of claim 1 which is tricyclo[3.3.1.1$^{3,7}$]-decane-1-carboxylic acid 2-[4-(2-pyrimidinyl)-1-piperazinyl]ethyl ester, or a pharmaceutically acceptable salt thereof.

4. The compound of claim 1 which is tricyclo [3.3.1.1$^{3,7}$]-decane-1-carboxylic acid 3-[4-(2-methoxyphenyl)-1-piperizinyl]propyl ester, or a pharmaceutically acceptable salt thereof.

5. The compound of claim 1 which is 3-methyltricyclo-[3.3.1.1$^{3,7}$]decane-1-acetic acid 2-[4-(2-pyrimidinyl)-1-piperazinyl]ethyl ester, or a pharmaceutically acceptable salt thereof.

6. The compound of claim 1 which is 9H-fluorene-1-carboxylic acid 2-[4-(2-methoxyphenyl)-1-piperazinyl]ethyl ester, or a pharmaceutically acceptable salt thereof.

7. The compound of claim 1 which is 3-methyltricyclo-[3.3.1.1$^{3,7}$]decane-1-acetic acid 3-[4-[3-(trifluoromethyl)phenyl]-1-piperazinyl]propyl ester, or a pharmaceutically acceptable salt thereof.

8. The compound of claim 1 which is tricyclo[3.3.1.1$^{3,7}$]-decane-1-carboxylic acid 3-[4-(2-pyrimidinyl)-1-piperazinyl]propyl ester, or a pharmaceutically acceptable salt thereof.

9. The compound of claim 1 which is 9H-fluorene-1-carboxylic acid 2-[4-(3-chlorophenyl)-1-piperazinyl]ethyl ester, or a pharmaceutically acceptable salt thereof.

10. The compound of claim 1 which is tricyclo[3.3.1.1$^{3,7}$]-decane-1-carboxylic acid 3-[4-[bis(4-fluorophenyl)methylene]-1-piperidinyl]-propyl ester, or a pharmaceutically acceptable salt thereof.

11. The compound of claim 1 which is tricyclo[3.3.1.1$^{3,7}$]-decane-1-carboxylic acid [2-[4-(2-cyanophenyl)-1-piperazinyl]ester, or a pharmaceutically acceptable salt thereof.

12. The compound of claim 1 which is tricyclo[3.3.1.1$^{3,7}$]-decane-1-carboxylic acid 2-[4-[bis(4-fluorophenyl)methylene]-1-piperidinyl]-ethyl ester, or a pharmaceutically acceptable salt thereof.

13. The compound of claim 1 which is tricyclo[3.3.1.1$^{3,7}$]-decane-3-methyl-1-acetic acid 2-[4-[bis(4-fluorophenyl]methylene]-1-piperidinyl]ethyl ester, or a pharmaceutically acceptable salt thereof.

14. The compound of claim 1 which is tricyclo[3.3.1.1$^{3,7}$]-decane-3-methyl-1-acetic acid 2-[4-(4-fluorophenyl)hydroxymethyl]-1-piperidinyl]ethyl ester, or a pharmaceutically acceptable salt thereof.

* * * * *